(12) United States Patent
Perkins

(10) Patent No.: US 7,596,209 B2
(45) Date of Patent: Sep. 29, 2009

(54) MULTI-LEAF COLLIMATOR

(75) Inventor: Clifford William Perkins, Crawley (GB)

(73) Assignee: Elekta AB (publ), Stockholm (SE)

( * ) Notice: Subject to any disclaimer, the term of this patent is extended or adjusted under 35 U.S.C. 154(b) by 0 days.

(21) Appl. No.: 11/885,571

(22) PCT Filed: Feb. 28, 2006

(86) PCT No.: PCT/GB2006/000696

§ 371 (c)(1),
(2), (4) Date: Sep. 4, 2007

(87) PCT Pub. No.: WO2006/092575

PCT Pub. Date: Sep. 8, 2006

(65) Prior Publication Data

US 2008/0165930 A1    Jul. 10, 2008

(30) Foreign Application Priority Data

Mar. 4, 2005    (GB) .................................. 0504486.2

(51) Int. Cl.
*G21K 1/04*    (2006.01)
(52) U.S. Cl. .................... 378/152; 378/149; 378/150
(58) Field of Classification Search .......... 378/147–152; 250/505.1
See application file for complete search history.

(56) References Cited

U.S. PATENT DOCUMENTS

| | | | |
|---|---|---|---|
| 6,730,924 B1 * | 5/2004 | Pastyr et al. | 250/505.1 |
| 6,823,045 B2 * | 11/2004 | Kato et al. | 378/152 |
| 2004/0062353 A1 | 4/2004 | Kato et al. | |
| 2004/0240621 A1 | 12/2004 | Noguchi | |

* cited by examiner

*Primary Examiner*—Jurie Yun
(74) *Attorney, Agent, or Firm*—Lahive & Cockfield, LLP; Anthony A. Laurentano, Esq.

(57) ABSTRACT

A multi-leaf collimator comprises an elongate leaf moveable in a longitudinal direction, and having an associated toothed rack driven by a pinion, wherein the rack is carried on an elongate actuator section, having a transversely extending link section, the leaf being connected to the link section and thereby being spaced from the actuator section.

7 Claims, 6 Drawing Sheets

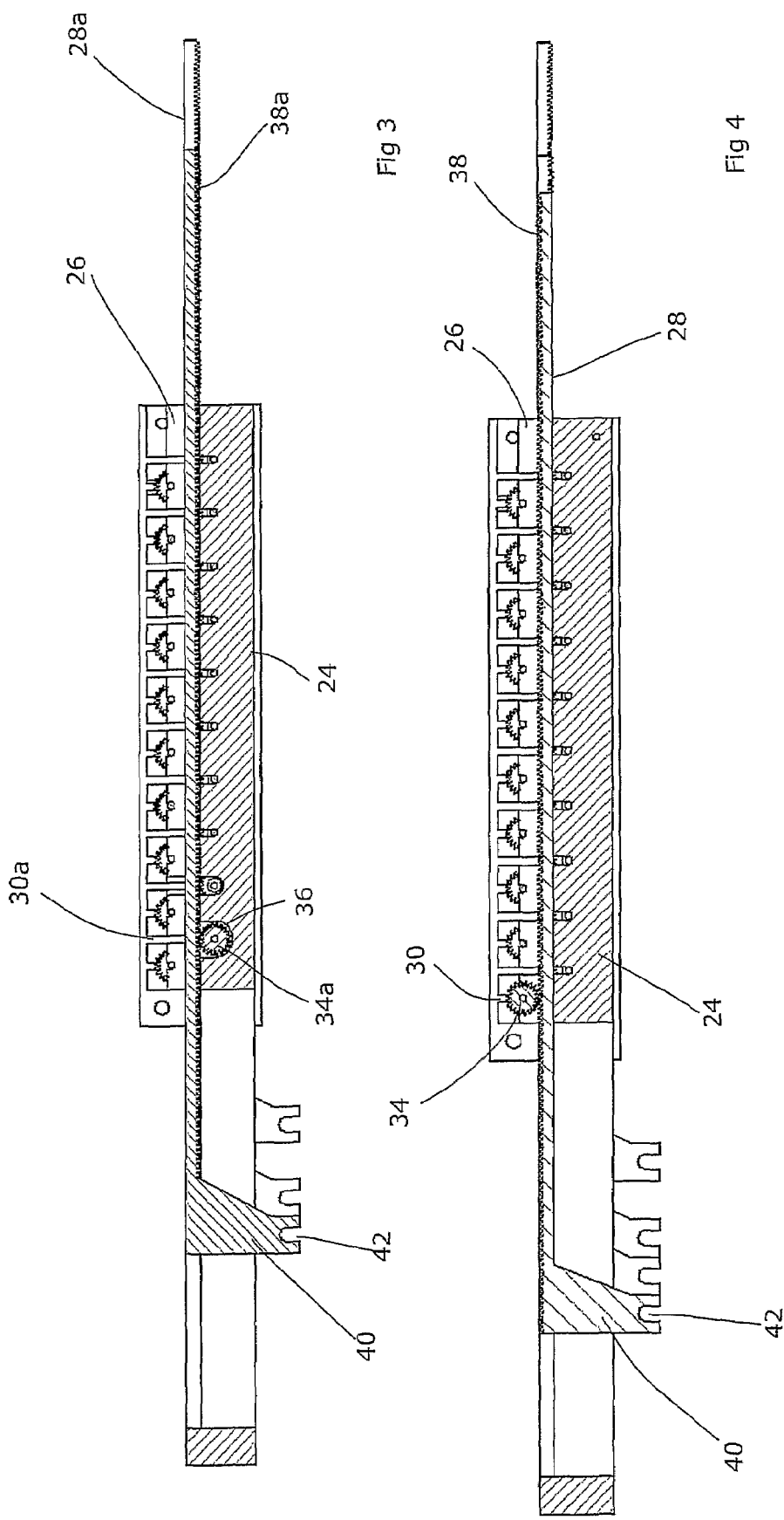

MULTI-LEAF COLLIMATOR

FIELD OF THE INVENTION

The present invention relates to a multi-leaf collimator.

BACKGROUND ART

Multi-leaf collimators (MLC) are used (principally) in the field of radiotherapy. A beam of radiation is directed toward a patient and must be collimated to fit the shape of the area to be treated. It is important to ensure that the dose in the areas outside that shape is as low as possible, but also that the whole area is treated. If areas are left untreated then the likelihood of recurrence is increased, whereas if non-treatment regions are irradiated then damage will be caused to healthy tissue resulting in greater side effects and longer recovery times after treatment.

As the treatment area is rarely rectilinear, multi-leaf collimators are employed. These comprise an array of finger-shaped leaves of a radiation-absorbing material, each disposed in a parallel relationship and each able to move longitudinally relative to the others. By moving each leaf to a selected position, a collimator is provided which can exhibit a non-linear edge. In general, one such array (or "bank") will be provided on each side of the beam.

Previously, the leaves have been driven by various means. One involves a threaded shaft extending rearwardly away from the leaf; this can be supported in a threaded bore or connected to the leaf via a threaded socket. In either case, as the shaft or bore is rotated the leaf will be forced to move. An example is shown at U.S. Pat. No. 4,868,844 in which motors are placed to one side and linked to the threaded shafts by a flexible shaft. Activation of the motor under microprocessor control forces the threaded shaft to rotate and move through the threaded bore in which it is held. This then urges the leaf in the appropriate direction. The use of flexible shafts allows the motors to be spatially separated from the leaves and allows for the facts that the motors are significantly wider than the leaves.

A further example is shown in FIG. 9. The leaf 200 is supported on its lower edge by a roller bearing 202, and is guided along its upper edge by a pair of roller bearings 204, 206. A longitudinal slot 208 is cut into the leaf, extending from the rear edge 210 towards the front edge 212. At the start of the slot 208, proximate the rear edge 210, a threaded nut 214 is fixed in place, in line with the slot. A leadscrew 216 is then threaded through the nut 214 and sits in the slot 208.

A motor and gearbox 218 are positioned behind the leaf and drive the leadscrew 216 via a shaft support and coupling 220. Thus, as the leadscrew is driven, the nut 214 and hence the leaf 200 will be driven rearwardly or forwardly, depending on the direction of rotation.

Other designs use a rack and pinion system, where a toothed rack is cut into the edges of the leaves, and motors are mounted outboard of the leaves with a drive shaft that extends perpendicular to the leaves, across the bank. Each shaft carries a pinion at the relevant location so as to engage with the rack of the appropriate leaf.

Multi leaf collimators are now being designed with smaller resolution leaves which are therefore thinner and more numerous. A significant problem in doing so is the need to drive the leaves, i.e. provide a means of physically moving them to the required degree of accuracy, and the impact of this on the length of a leafbank, the length of a leaf, and its the complexity and serviceability. This in turn increases the size of the treatment head and can restrict the patient treatment access.

If the leaves are driven from one end, then the motors are outboard and undesirably add length to the assembly. Likewise, reductions in the leaf width mean that it becomes increasingly difficult to embed a leadscrew.

The existing rack & pinion methods also become increasingly difficult with a larger number of leaves, and usually result in extending the leaf length in order to accommodate the necessary number of motor drives.

SUMMARY OF THE INVENTION

The present invention therefore provides a multi-leaf collimator, comprising an elongate leaf moveable in a longitudinal direction, and having an associated toothed rack driven by a pinion, wherein the rack is carried on an elongate actuator section, having a transversely extending link section, the leaf being connected to the link section and thereby being spaced from the actuator section.

The actuator section can be formed integrally with the leaf, but we prefer it to be joined to the leaf, particularly if joined in a manner that is detachable.

The multi-leaf collimator will generally comprise a plurality of such leaves arranged in an array. We then prefer that at least one leaf of the plurality has a rack formed on an edge of the respective actuator section proximate the respective leaf. The pinion which drives that leaf will then be located between the actuator section and the leaf. The pinion can thus be mounted on a shaft which is disposed transversely to the leaves of the array, and which passes between those leaves and their respective actuators.

That or other leaves can also have a rack formed on an edge of the actuator section distal the respective leaf. Thus, some leaves can be driven via pinions mounted on shafts passing over the array, and other leaves can be driven via pinions mounted on shafts passing within the gaps between leaves and actuators. This means that twice the number of drive shafts can be fitted into the same length of array, thus either shortening the array or permitting more leaves and hence greater resolution.

The drive mechanism can also be made as a separate unit. Thus, the invention further provides a drive mechanism for a multi-leaf collimator, comprising an elongate actuator section for each leaf of the collimator, the actuator being moveable in a longitudinal direction and having a toothed rack driven by a pinion, and a transversely extending link section, the link section have an engagement means for connection with a leaf, thereby to space the leaf from the actuator section.

A separate drive unit is advantageous in manufacturing as it allows the drive unit to be produced, built and tested as a separate assembly in a specialist environment. Service replacement of the entire gearbox in the event of a fault will also be swifter, with minimal re-setting. It is likely that the replacement of such a gearbox will take considerably less time than the replacement of the sum of individual component parts that constitute existing drive technologies.

Further, the gearbox will be an enclosed unit, with integral lubrication and shielded from environmental dust and debris.

The invention also offers a major advantage in the leaf length is no longer dictated by the length of the rack. The leaf can be made smaller, saving material and reducing its weight. That reduction in weight will make movement of the leaf easier, improving both accuracy and reliability.

BRIEF DESCRIPTION OF THE DRAWINGS

An embodiment of the present invention will now be described by way of example, with reference to the accompanying figures in which;

FIGS. 3 and 4 show sections through the drive mechanism;

DETAILED DESCRIPTION OF THE EMBODIMENTS

Figure 1:
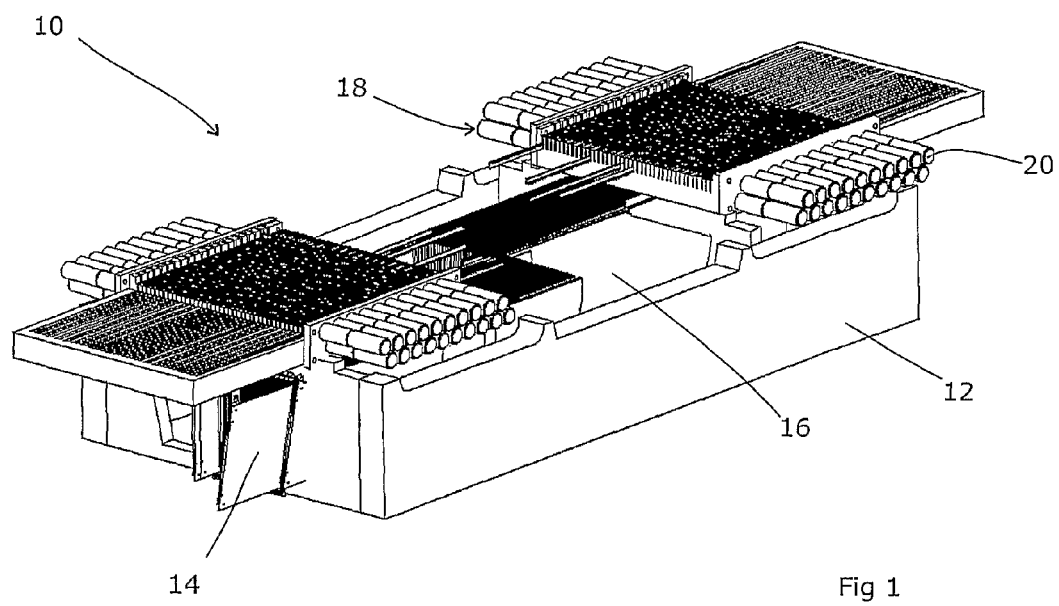
FIG. 1 is a perspective view of a multi-leaf collimator according to the present invention.

FIG. 1 shows a multi-leaf collimator 10. A housing 12 contains two opposing arrays of elongate leaves 14, a selection of which are shown in FIG. 1. These leaves 14 are each moveable longitudinally within the array so that they can each project by a greater or lesser distance into the open space 16 disposed generally in the middle of the housing 12. In use, a beam of radiation is directed through that open space 16 and its extent is collimated by the leaves 14. The leaves are relatively thin so as to allow a high resolution to be obtained, but they are relatively deep in the direction of the beam in order to render them fully opaque at X-ray energies. The leaves 14 are relatively elongate so as to allow them to adopt a wide range of positions.

For each array of leaves 14, there is a drive unit 18. This has arrays of motors 20 on either side, each of which is associated with an individual leaf. A suitable micro-processor will typically be provided (not shown) which will provide power to the required motors in order to move the appropriate leaf or leaves and provide the required collimation. However, this requires that the motors be operatively connected to the relevant leaf.

Figure 2:
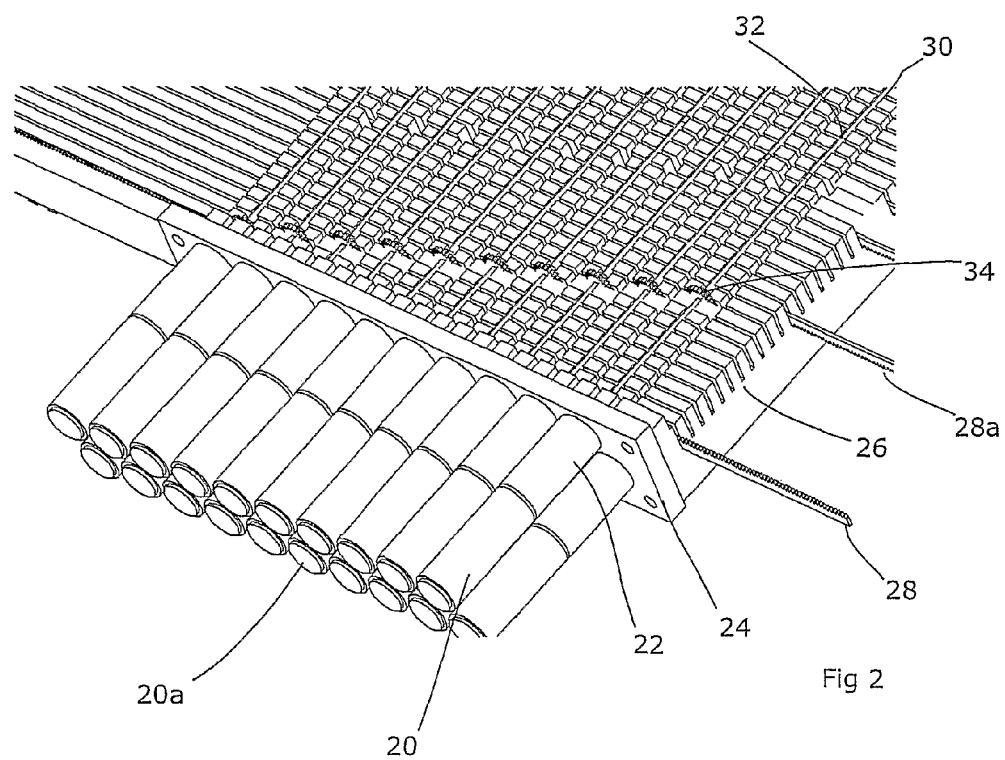
FIG. 2 shows in detail part of the drive mechanism of FIG. 1.

FIG. 2 shows general how this is achieved. Each motor 20 has an in-line gear box 22 which is mounted to the side of the drive housing 24. The drive housing 24 has a series of slots 26 in which are disposed actuator sections 28 in a slideable manner. That is, the actuator section 28 can slide longitudinally within the slot 26. Transverse channels 30 are formed in the drive housing 24, running perpendicularly to the slots 26 albeit somewhat shallower. Drive shafts 32 are located in the transverse channels 30 and are driven by the gearboxes 22. Thus, each motor 20 drives an in-line gearbox 22, which drives an in-line drive shaft 32 lying in a channel 30. On each drive shaft 32 there is a single pinion 34 which thus lies within a slot 26. The pinion 34 has teeth which engage with a rack cut into one edge of the actuator section 28. Thus, each motor 20 drives a particular actuator shaft 28.

It will seem from FIG. 2 that the motors 20 are arranged in two banks. An upper bank powers drive shafts 32 that are located in shallow transverse channels 30. Pinions 34 located on these shafts 32 drive an actuator section 28 that is disposed beneath the pinion, and which therefore has a rack formed on its upper surface.

The remaining motors 20A are disposed beneath the above-described motors 20, in a staggered configuration. These power drive shafts 32 located in relatively deeper transverse channels 30, and drive pinions 34 that are located beneath the relevant actuator section 28. Thus, such actuator sections 28A have a rack that is cut into their lower edge.

This can be seen more clearly in FIGS. 3 and 4. Both are sections through the drive unit at a slot 26, but FIG. 3 is a section at a slot containing an actuator section driven from beneath whereas FIG. 4 is a section at a slot containing an actuator section driven from above.

Referring to FIG. 3, this shows a deeper transverse channel 30a in which lies a drive shaft on which is mounted a pinion 34a. The pinion 34a sits in a recess 36 created at the foot of the transverse channel 30a to allow the pinion 34a to rotate. The actuator section 28a is placed in the slot 26, above the pinion 34a, and has a rack 38a on its lower edge. Thus, as the motor 20a drives the relevant gear box and drive shaft 32a, the pinion 34a rotates and the actuator section 28a moves linearly and in a longitudinal direction.

Likewise, as can be seen from FIG. 4, the adjacent motor 20 drives a shaft 32 in a transverse recess 30 that is somewhat more shallow. A pinion 34 is mounted on that drive shaft 30 and engages with a rack 38 formed on the upper surface of an actuator section 28. That actuator section sits in a slot 26 that is the same depth as the slot 26 illustrated in FIG. 3, and therefore all the actuated sections line up. However, the lesser depth of the transverse channel 30 in which the drive shaft 32 is placed means that that pinion 34 correctly engages with the rack 38 on the upper surface of the actuator section 28.

In this way, by staggering the motors and pinions 34, a greater number of drives can be incorporated into the same length of housing 24. This therefore means that the housing 24 can be made shorter, thereby reducing the overall size of the MLC drive, or it means that a greater number of leaves can be fitted into the same size drive thereby increasing resolution.

As can be seen in FIGS. 3 and 4 each actuator section 28 has an associated link section 40. This is formed integrally with the actuator section 28 and extends downwardly towards the array of leaves 14. At its tip there is an engagement section 42 which fits within a corresponding formation on the leaf 14. Thus, the gearbox can be fitted in place over a leaf array and the relevant link sections will engage with the appropriate leaf. Thus, as the actuator section is moved linearly, the link section 40, 42 will drag the relevant leaf 14 with it.

Figure 5:
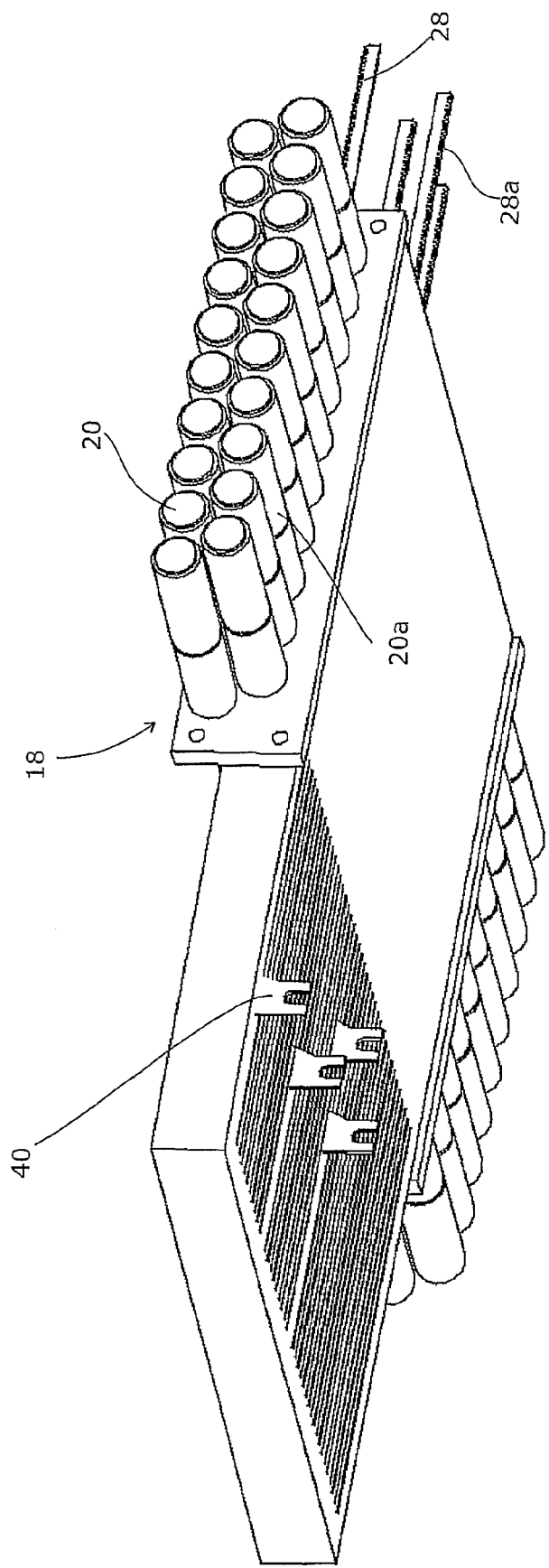
FIG. 5 shows the drive unit from beneath.

FIG. 5 shows the drive mechanism 18 from below. The structure described with reference to FIGS. 2, 3 and 4 is duplicated on either side of the device, thereby still further minimizing the necessary length of the unit. For clarity, only a minority of the link sections 40 are shown.

Figure 6:
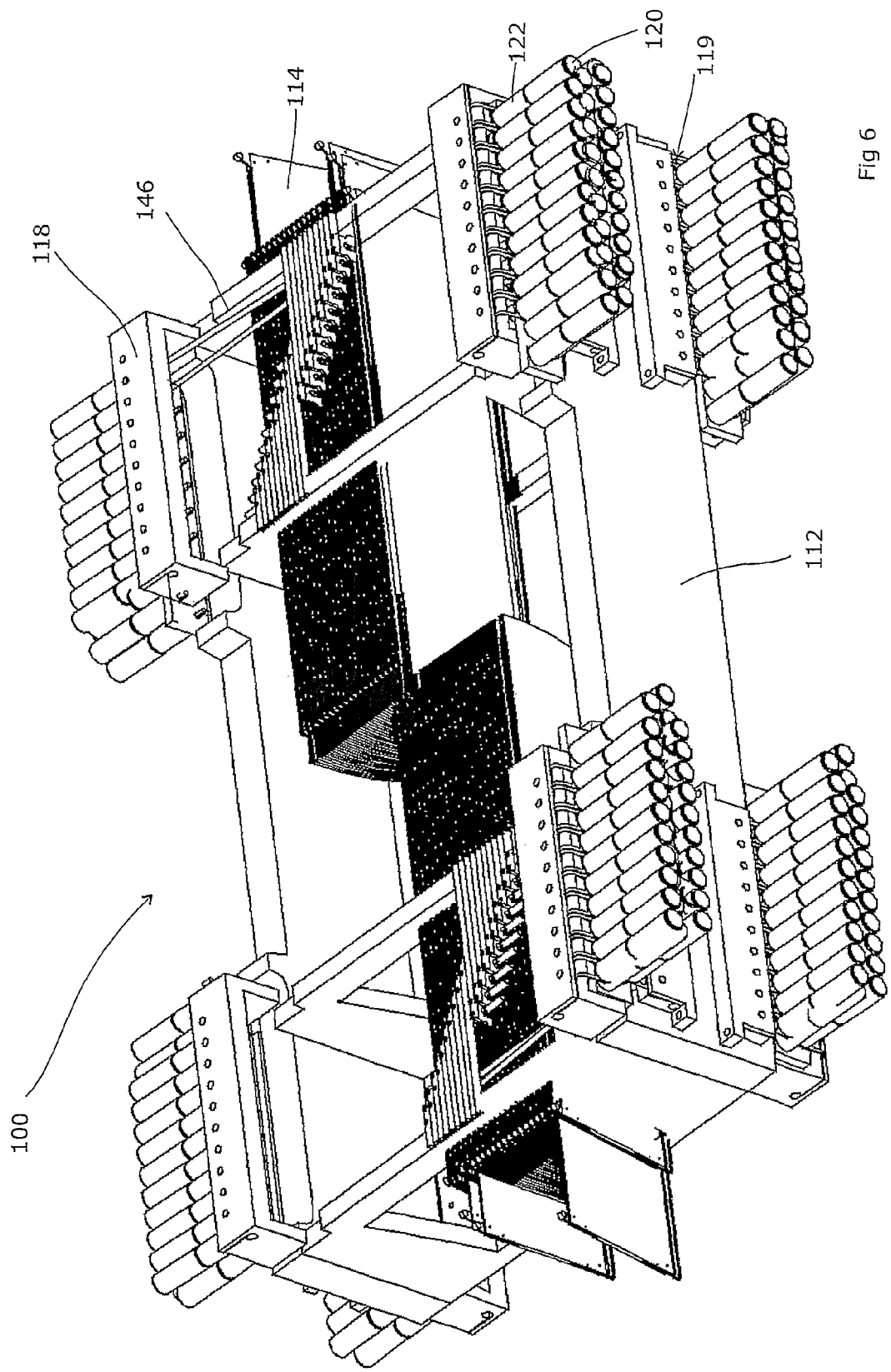
FIG. 6 shows an alternative embodiment, in use.

FIG. 6 shows an alternative device. In this arrangement, each of the two opposing banks of leaves 114 is associated with a pair of gear boxes 118, 119. These are mounted on the respective upper and lower faces of the housing 112, and each drive unit powers one half of the leaves 114 (of which a selection are illustrated only, for clarity). Thus, this allows the necessary length of the device to be reduced still further, or (alternatively), permits a greater number of leaves to be incorporated for the same size of device. In a further alternative, this allows the actuator sections 128 and pinions 134 etc. to be constructed of a heaver gage material and therefore made somewhat more robust. Each actuator section 128 on (for example) the upper drive section 118 can drive alternate leaves 114 of the array. The remaining leaves of 114 can be driven by the drive section 119 located on the lower section of the housing 112.

Figure 7:
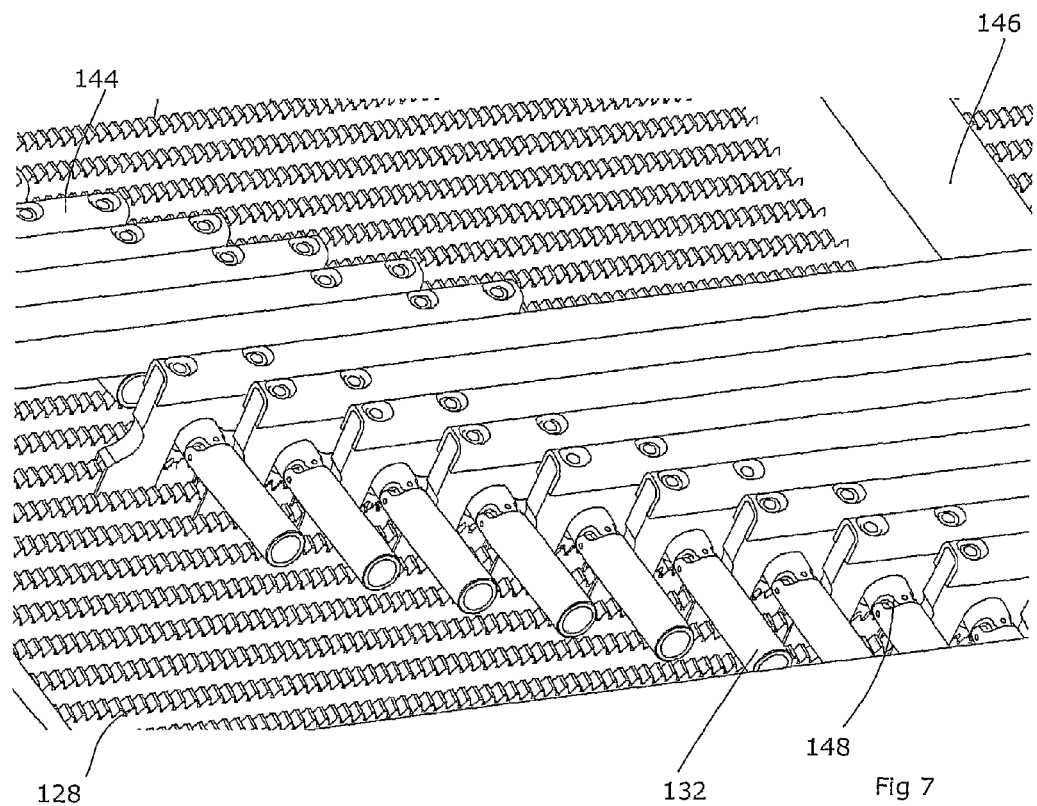
FIGS. 7 and 8 show the drive mechanisms of FIG. 7 in detail.
Figure 8:
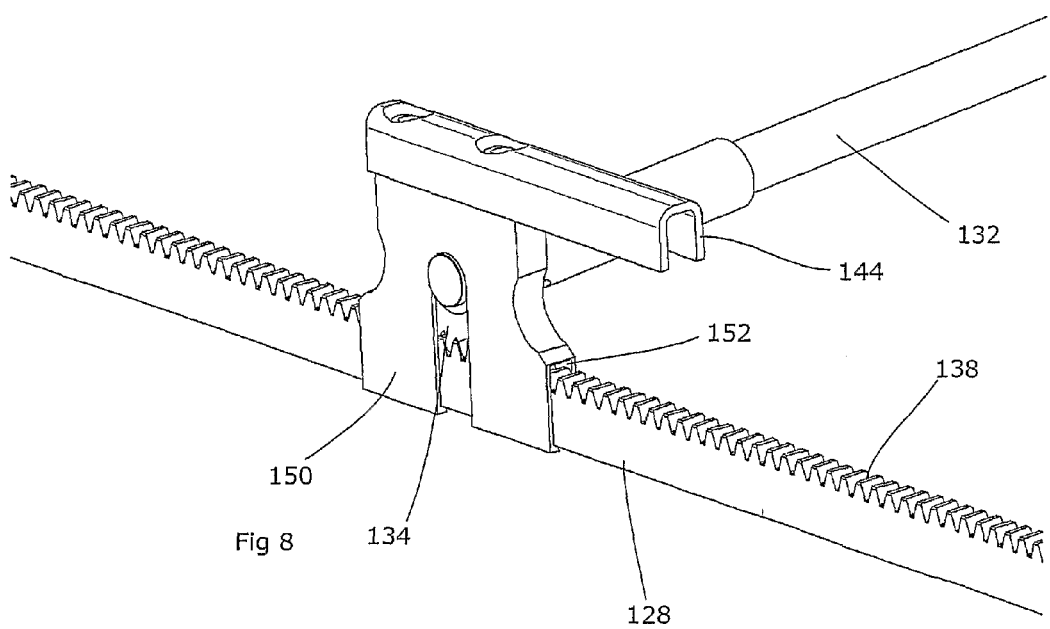
Figure 9:
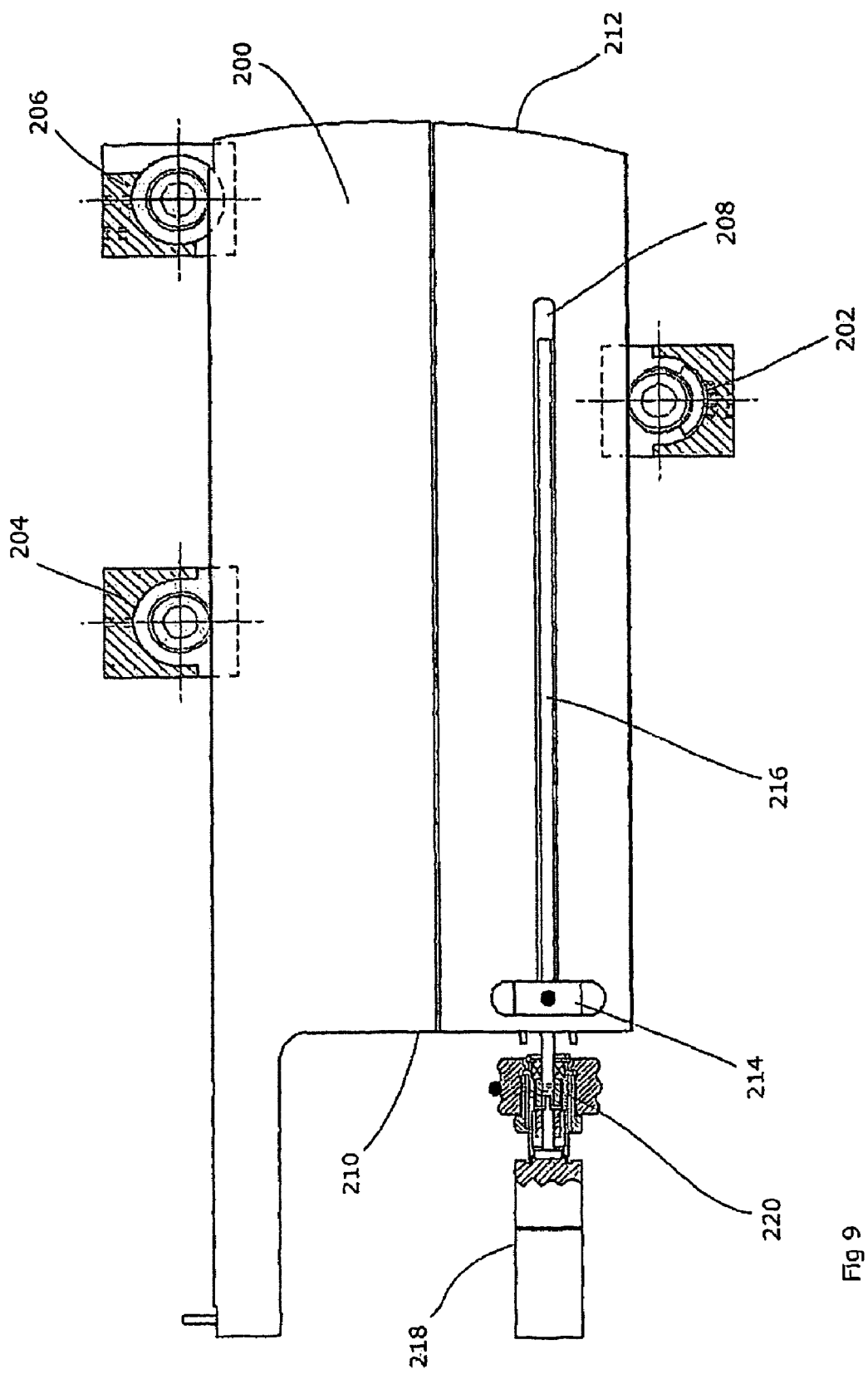
FIG. 9, described above, shows an existing design of collimator leaf.

FIGS. 7 and 8 show such an alternative construction for the actuated sections 128 etc. A channel section 144 extends in line with and above the relevant leaf 114, supported at one or both ends by a cross member 146. The drive shaft 132 extends from the gear box 122 and drives the pinion 134 via a universal joint 148, to allow for production tolerances. The pinion 134 is housed within a sleeve 150 attached to the channel section 144 and depending downwardly thereof. This envelopes the pinion 134 and includes a suitably sized rectangular bore 152 through which the actuated section 128 passes. Thus, the pinion 134 meshes with the rack 138 formed on the edge of the actuated section 128 and the motor 120 is able to drive the actuator section 128.

A corresponding but inverted mechanism is provided for those actuated sections 128 that are driven from beneath.

It will of course be understood that many variations may be made to the above-described embodiment without departing from the scope of the present invention.

The invention claimed is:

1. A multi-leaf collimator, comprising an elongate leaf moveable in a longitudinal direction, and having an associated toothed rack driven by a pinion,
   characterized in that;
   the rack is carried on an elongate actuator section, having a transversely extending link section,
   the leaf being connected to the link section and thereby being spaced from the actuator section; the actuator section and the leaf being detachable.

2. A multi-leaf collimator according to claim 1 in which the actuator section is joined to the leaf.

3. A multi-leaf collimator comprising a plurality of leaves arranged in an array, each leaf being according to claim 1, in which at least one leaf of the plurality has a rack formed on an edge of the respective actuator section proximate the respective leaf.

4. A multi-leaf collimator according to claim 3 in which the pinion which drives the at least one leaf is located between the actuator section and the leaf.

5. A multi-leaf collimator according to claim 4 in which the pinion is mounted on a shaft which is disposed transversely to the leaves of the array and which passes between those leaves and their respective actuators.

6. A multi-leaf collimator comprising a plurality of leaves arranged in an array, each leaf being according to claim 1, in which at least one leaf of the plurality has a rack formed on an edge of the actuator section distal the respective leaf.

7. A drive mechanism for a multi-leaf collimator, comprising an elongate actuator section for each leaf of the collimator, the actuator being moveable in a longitudinal direction and having a toothed rack driven by a pinion, and a transversely extending link section, the link section have an engagement means for connection with a leaf, thereby to space the leaf from the actuator section.

* * * * *